United States Patent
Kazama et al.

(10) Patent No.: US 10,988,688 B2
(45) Date of Patent: Apr. 27, 2021

(54) METHOD FOR MANUFACTURING QUANTUM DOT

(71) Applicant: STANLEY ELECTRIC CO., LTD., Tokyo (JP)

(72) Inventors: Takuya Kazama, Tokyo (JP); Wataru Tamura, Yokohama (JP); Yasuyuki Miyake, Tokyo (JP)

(73) Assignee: STANLEY ELECTRIC CO., LTD., Tokyo (JP)

( * ) Notice: Subject to any disclaimer, the term of this patent is extended or adjusted under 35 U.S.C. 154(b) by 688 days.

(21) Appl. No.: 15/666,557

(22) Filed: Aug. 1, 2017

(65) Prior Publication Data

US 2017/0355903 A1 Dec. 14, 2017

Related U.S. Application Data

(63) Continuation of application No. PCT/JP2016/000279, filed on Jan. 20, 2016.

(30) Foreign Application Priority Data

| Feb. 2, 2015 | (JP) | JP2015-018477 |
| Feb. 6, 2015 | (JP) | JP2015-021936 |
| Feb. 6, 2015 | (JP) | JP2015-021937 |

(51) Int. Cl.

| *C09K 11/64* | (2006.01) |
| *C09K 11/08* | (2006.01) |
| *C09K 11/56* | (2006.01) |
| *H01L 33/32* | (2010.01) |
| *C09K 11/62* | (2006.01) |
| *C09K 11/02* | (2006.01) |
| *B82Y 5/00* | (2011.01) |
| *C30B 7/14* | (2006.01) |
| *C30B 29/40* | (2006.01) |
| *H01L 33/50* | (2010.01) |
| *B82Y 20/00* | (2011.01) |
| *B82Y 40/00* | (2011.01) |

(52) U.S. Cl.
CPC ............ *C09K 11/642* (2013.01); *B82Y 5/00* (2013.01); *C09K 11/02* (2013.01); *C09K 11/08* (2013.01); *C09K 11/0883* (2013.01); *C09K 11/565* (2013.01); *C09K 11/62* (2013.01); *C09K 11/64* (2013.01); *C30B 7/14* (2013.01); *C30B 29/403* (2013.01); *H01L 33/32* (2013.01); *B82Y 20/00* (2013.01); *B82Y 40/00* (2013.01); *H01L 33/502* (2013.01); *Y10S 977/774* (2013.01); *Y10S 977/817* (2013.01); *Y10S 977/824* (2013.01); *Y10S 977/892* (2013.01); *Y10S 977/95* (2013.01)

(58) Field of Classification Search
CPC ............ C09K 11/64; C09K 11/11642; C09K 11/0883; C09K 11/642; B82Y 20/00; B82Y 40/00; Y10S 977/774

See application file for complete search history.

(56) References Cited

U.S. PATENT DOCUMENTS

| 7,211,143 | B2 | 5/2007 | Yang et al. |
| 7,892,452 | B2 | 2/2011 | Ryowa et al. |
| 9,478,700 | B2 | 10/2016 | Daniels et al. |
| 9,773,942 | B2 | 9/2017 | Kazama et al. |
| 10,032,955 | B2 | 7/2018 | Kazama et al. |
| 2003/0057415 | A1 | 3/2003 | Komori |
| 2004/0175844 | A1 | 9/2004 | Yang et al. |
| 2005/0224785 | A1 | 10/2005 | Komori |
| 2007/0037365 | A1 | 2/2007 | Ranganath et al. |
| 2010/0163798 | A1 | 7/2010 | Ryowa et al. |
| 2010/0187497 | A1 | 7/2010 | Nago et al. |
| 2010/0283005 | A1 | 11/2010 | Pickett et al. |
| 2011/0263129 | A1 | 10/2011 | Shin et al. |
| 2013/0270517 | A1 | 10/2013 | Nozawa et al. |
| 2014/0252316 | A1* | 9/2014 | Yan .................... C09K 11/02 257/24 |
| 2014/0264172 | A1 | 9/2014 | Daniels et al. |
| 2015/0194577 | A1 | 7/2015 | Glarvey et al. |
| 2016/0211409 | A1 | 7/2016 | Kazama et al. |
| 2017/0009134 | A1 | 1/2017 | Daniels et al. |
| 2017/0218268 | A1 | 8/2017 | Pickett et al. |
| 2017/0373223 | A1 | 12/2017 | Kazama et al. |
| 2018/0047878 | A1 | 2/2018 | Glarvey et al. |
| 2020/0052169 | A1 | 2/2020 | Glarvey et al. |

FOREIGN PATENT DOCUMENTS

| CN | 105899640 A | 8/2016 |
| EP | 3050936 A1 | 8/2016 |
| JP | 2003107546 A | 4/2003 |
| JP | 2007050500 A | 3/2007 |
| JP | 4318710 B2 | 8/2009 |
| JP | 4502758 B2 | 7/2010 |
| JP | 2011076827 A | 4/2011 |
| JP | 2011258994 A | 12/2011 |
| JP | 4936338 B2 | 5/2012 |
| JP | 2012087220 A | 5/2012 |
| JP | 2013239690 A | 11/2013 |

OTHER PUBLICATIONS

Japanese Office Action (and English language translation thereof) dated Dec. 10, 2019 issued in counterpart Japanese Application No. 2016-008999.
International Search Report (ISR) and Written Opinion dated Apr. 12, 2016 issued in International Application No. PCT/JP2016/000279.
Extended European Search Report (EESR) dated Jul. 31, 2018 issued in counterpart European Application No. 16746269.6.
Chinese Office Action (and English translation thereof) dated Jan. 3, 2020, issued in counterpart Chinese Application No. 201680008020.0.

* cited by examiner

*Primary Examiner* — Edward M Johnson
(74) *Attorney, Agent, or Firm* — Holtz, Holtz & Volek PC

(57) ABSTRACT

A quantum dot manufacturing method comprises (a) dispersing, in a solvent, nano-seed particles whose crystal planes are exposed, and (b) growing semiconductor layers on the exposed crystal planes of the nano-seed particles in the solvent.

15 Claims, 8 Drawing Sheets

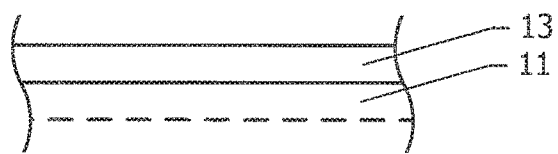
FIG. 5A
FIG. 5B
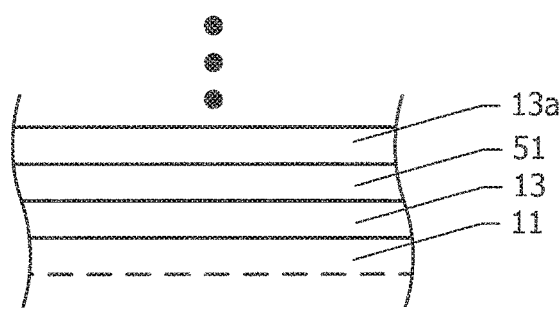
FIG. 5C
FIG. 5D
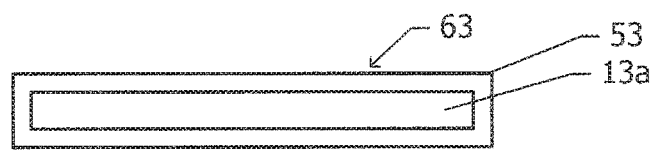
FIG. 5E
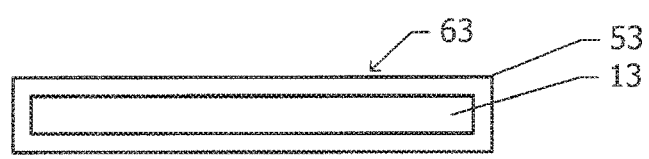

METHOD FOR MANUFACTURING QUANTUM DOT

FIELD OF THE INVENTION

The present invention relates to a quantum dot manufacturing method and a quantum dot.

BACKGROUND

A substance made as small (fine or thin) as about several nanometers up to less than 20 nanometers in size begins to exhibit physical properties different from those in its bulk state. This phenomenon or effect is called a (three to one dimensional) carrier confinement effect or a quantum size effect, and a substance that displays such an effect is called a quantum dot (quantum wire or quantum well) or a semiconductor nanoparticle, for example. The bandgap (optical absorption wavelength or emission wavelength) of a quantum dot can be adjusted by changing the size (overall size) of the quantum dot.

One usage of a quantum dot containing a semiconductor material is a fluorescent material. A quantum dot containing a semiconductor material can emit florescence of a particular wavelength when irradiated with high-energy light or particle radiation. An area light source can be obtained by evenly distributing quantum dots and causing the quantum dots to emit light.

Quantum dots having a core-shell structure in which a core (nucleus) portion is covered with a shell layer are available (for example, Japanese Laid-open Patent Publication Nos. 2011-076827 and 2012-087220, and Japanese Patent Nos. 4936338 and 4318710). These quantum dots can be manufactured by, for example, a liquid phase growth method (for example, Japanese Patent Nos. 4936338, 4318710 and 4502758).

SUMMARY

A main object of the present invention is to obtain a quantum dot having a novel structure. Another object of the present invention is to obtain a quantum dot that has high reliability and excellent efficiency. Yet another object of the present invention is to efficiently manufacture quantum dots.

According to an aspect of this invention, there is provided a quantum dot manufacturing method comprising (a) dispersing, in a solvent, nano-seed particles whose crystal planes are exposed, and (b) growing semiconductor layers on the exposed crystal planes of the nano-seed particles in the solvent.

A quantum dot having a novel structure (flat multilayer structure) and a quantum dot having high reliability and excellent efficiency can be obtained through the present invention. Moreover, quantum dots can be manufactured more efficiently.

BRIEF DESCRIPTION OF THE DRAWINGS

FIGS. 5A to 5E are schematic cross-sectional views of a quantum dot manufacturing process according to a third embodiment.

DESCRIPTION OF THE PREFERRED EMBODIMENTS

First Embodiment

Quantum dots in the visible light spectrum used presently are CdSe/ZnS, InP/ZnS, and the like in which a shell having a large energy gap is stacked on a core having a small energy gap. When a core-shell structure is configured by using different compound materials, lattice mismatch (CdSe/ZnS: 11.1%, InP/ZnS: 7.8%) occurs. Lattice mismatch can cause deformation of crystal lattices and degradation of emission efficiency and reliability.

Figure 1:
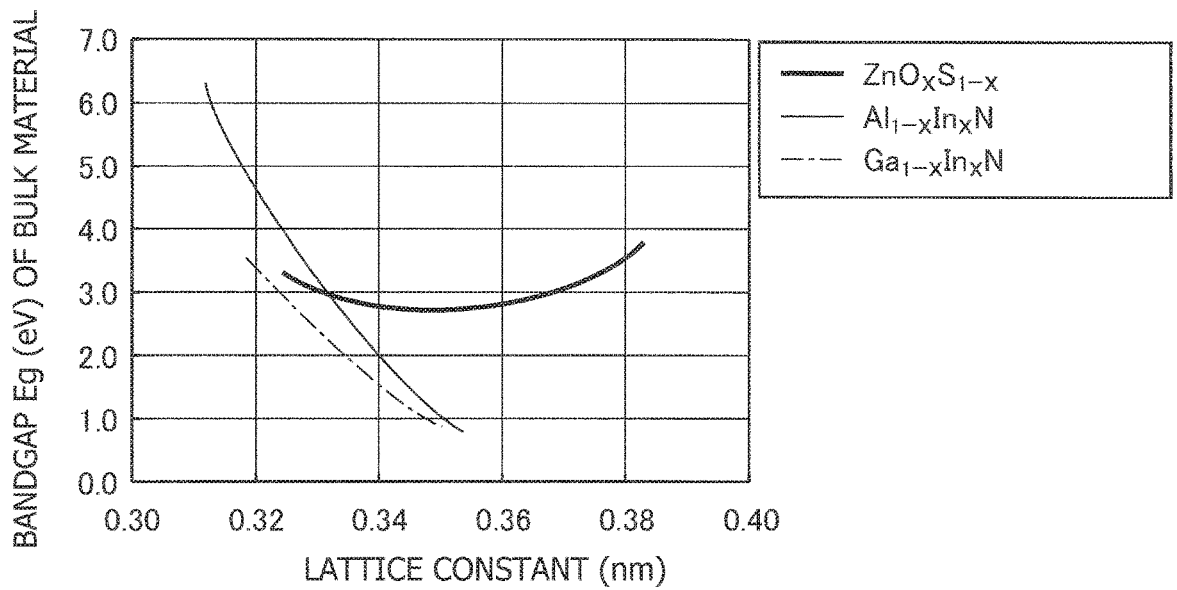
FIG. 1 is a graph showing the relationships between lattice constants of a ZnOS mixed crystal system, a GaInN mixed crystal system, and an AlInN mixed crystal system, and the energy gap.

FIG. 1 is a graph showing the relationships between the lattice constants of a ZnOS mixed crystal system, a GaInN mixed crystal system, and an AlInN mixed crystal system, and the energy gap. The term "mixed crystal system" refers to a system that contains a mixed crystal containing two end members and intermediate members. The horizontal axis indicates the lattice constant in terms of nanometers (nm), and the vertical axis indicates the energy gap in terms of electron volt (eV). The energy gaps that determine the emission wavelength are ZnO: 3.2 eV, ZnS: 3.8 eV, AlN: 6.2 eV, GaN: 3.4 eV, and InN: 0.64 eV.

In growing hexagonal crystals in the c-axis direction, the a-axis lattice constant is used as the lattice constant within the plane of growth. The a-axis lattice constants of ZnO and ZnS are, respectively, 0.324 nm and 0.382 nm. The a-axis lattice constants of AlN, GaN, and InN are, respectively, 0.311 nm, 0.320 nm, and 0.355 nm.

In pairing the compounds, a combination with the closest lattice constants is ZnO having a lattice constant of 0.324 nm and GaN having a lattice constant of 0.320 nm, and lattice mismatch exceeding 1% is present even with this combination.

Figure 2:
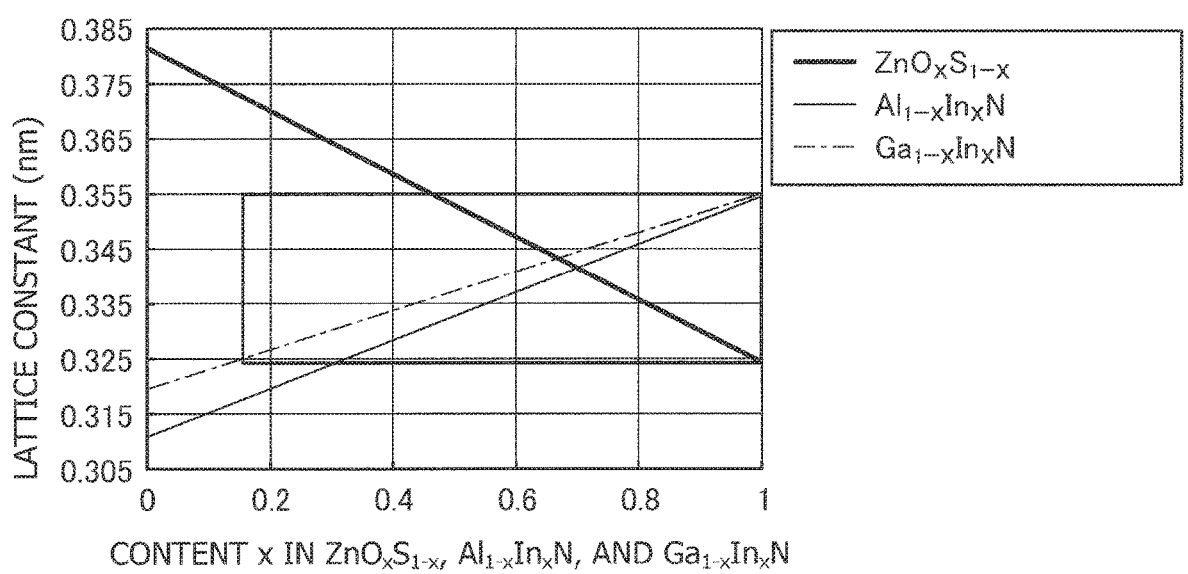
FIG. 2 is a graph showing changes in lattice constants of a $ZnO_xS_{1-x}$ mixed crystal system, a $Ga_{1-x}In_xN$ mixed crystal system, and an $Al_{1-x}In_xN$ mixed crystal system relative to the content x.

FIG. 2 is a graph schematically showing changes in lattice constants (in the a-axis direction) of the $ZnO_xS_{1-x}$ mixed crystal system, the $Ga_{1-x}In_xN$ mixed crystal system, and the $Al_{1-x}In_xN$ mixed crystal system relative to the content x. The horizontal axis indicates the content x, and the vertical axis indicates the lattice constant. ZnOS and AlGaInN have the same hexagonal wurtzite crystal structure. When a mixed crystal is formed, the lattice constant can be adjusted to be some point between the two end members, and lattice matching can be achieved.

There is a particular relationship established between the lattice constant, the energy gap, and the content. FIG. 2 shows substantially the same information as that of FIG. 1. Which graph is to be used is determined according to the parameter focused. For example, the contents at which lattice matching is achieved are the contents at which the values along the vertical axis (lattice constant) are the same in FIG. 2. A preferable matching range of lattice matching would be a range in which the difference in lattice constant is within ±1.0% with reference to a smaller lattice constant (100%).

The region in which lattice matching is possible among $ZnO_xS_{1-x}$, $Al_{1-x}In_xN$, and $Ga_{1-x}In_xN$ is marked by a box. In the content range of $Al_{1-x}In_xN$ (x: 0.3 to 1.0), $Ga_{1-y}In_yN$ (y: 0.15 to 1.0), and $ZnO_zS_{1-z}$ (z: 0.47 to 1.0), lattice matching among ZnOS, AlInN, and GaInN is possible.

When ZnOS is used as a base crystal and AlGaInN that lattice-matches with ZnOS is grown on ZnOS, the strain at the interface can be reduced. Reducing strain prevents crystal defects, and a quantum dot with high efficiency would be achieved. Most crystals have properties that change depending on the crystal orientation. Obtaining a surface of a specified crystal plane orientation facilitates control of the properties. An epitaxial layer with controlled properties can be easily grown on a base particle when the base particle is processed to have a specified plane orientation.

A quantum dot having high reliability can be manufactured by using ZnOS, which is easy to manufacture, to form a base particle, performing etching to expose a specified plane (a specified crystal plane), and performing heteroepitaxy of lattice-matching AlGaInN crystals on the exposed surface. It is also possible to further grow other AlGaInN crystals thereon.

Figure 3A:
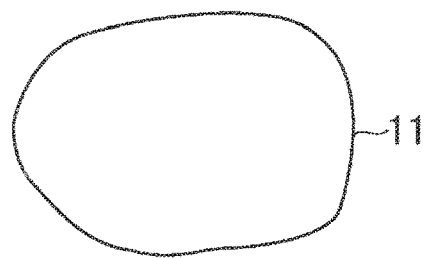
FIGS. 3A to 3D are schematic cross-sectional views of a quantum dot manufacturing process according to a first embodiment.
Figure 3B:
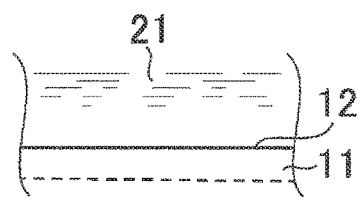
Figure 3C:
Figure 3D:
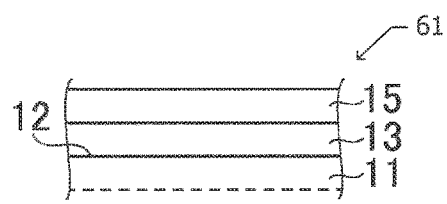

FIG. 3D is a schematic cross-sectional view of a quantum dot 61 according to the first embodiment. For example, an $In_{0.60}Ga_{0.40}N$ layer 13 having a (0001) surface is formed on a $ZnO_{0.72}S_{0.28}$ nano-seed particle 11 having a specified surface 12, which is a C (0001) plane, and an $In_{0.67}Al_{0.33}N$ layer 15 having a (0001) surface is formed on the $In_{0.60}Ga_{0.40}N$ layer 13. As illustrated in FIG. 2, $ZnO_{0.72}S_{0.28}$, $In_{0.60}Ga_{0.40}N$, and $In_{0.67}Al_{0.33}N$ are lattice-matched. The bandgap of each crystal satisfies the relationship, $In_{0.60}Ga_{0.40}N < In_{0.67}Al_{0.33}N < ZnO_{0.72}S_{0.28}$, as indicated in FIG. 1. The $In_{0.60}Ga_{0.40}N$ layer 13 functions as an emission layer, and the $ZnO_{0.72}S_{0.28}$ layer 11 and the $In_{0.67}Al_{0.33}N$ layer 15 on both sides function as barrier layers that transmit light emitted by band edge emission caused by carrier recombination. The (0001) plane orientations of the crystals are coincident, and desired properties are readily obtained.

Referring now to FIGS. 3A to 3D, an example of a quantum dot manufacturing method according to the first embodiment is described. Although one quantum dot is described, a large number of quantum dots are manufactured simultaneously by the liquid phase synthesis described below. The size of the quantum dots can be controlled by adjusting reaction conditions and the like. For example, the average particle diameter can be controlled to be 50 nm or less so that the particles can be suspended in a liquid phase.

First, a $ZnO_{0.72}S_{0.28}$ base particle is synthesized by hot injection.

Figure 8:
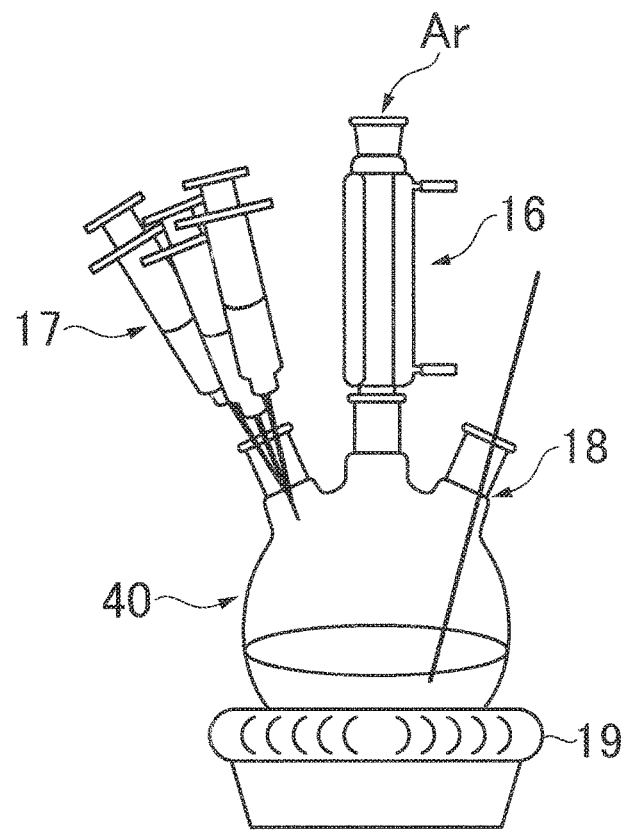
FIG. 8 is a schematic side view of an example of a reactor.

As illustrated in FIG. 8, a 300 ml quartz flask 40 is prepared as a reactor. The flask 40 is equipped with an outlet port, a port 16 through which inert gas purging is possible, multiple dedicated ports equipped with syringes 17 through which reaction precursors can be injected, and a temperature measuring unit 18 equipped with a thermocouple. Argon (Ar) is used as the inert gas. The flask 40 is placed on a heating mantle 19.

The syringes 17 respectively filled with reaction precursors, i.e., diethylzinc ($Zn(C_2H_5)_2$) sealed with inert gas, oxygen-bubbled octylamine ($C_8H_{17}NH_2$), and bis(trimethylsilyl) sulfide, are prepared. To obtain 4.0 mmol of diethylzinc, 2.8 mmol of oxygen-bubbled octylamine, and 1.2 mmol of bis(trimethylsilyl) sulfide, 410 µl of diethylzinc, 460 µl of octylamine, and 250 µl of bis(trimethylsilyl) sulfide are prepared. Oxygen-bubbled octylamine is prepared in advance by bubbling oxygen into octylamine for 2 minutes. The composition of the nano-particle can be changed by changing the ratios of the reaction precursors.

Into the reactor 40, 8 g of tri-n-octylphosphine oxide (TOPO) and 4 g of hexadecylamine (HDA) serving as a reaction solvent are placed. An inert gas (Ar) atmosphere is created, and the content is heated to 300° C. by using the heating mantle 19 while stirring with a stirrer to completely dissolve all components.

As soon as the reaction solvent reaches 300° C., the reaction precursors are quickly injected from the respective syringes. Due to pyrolysis of the reaction precursors, crystal nuclei of $ZnO_{0.72}S_{0.28}$ (wurtzite) are generated. Immediately after injection of the reaction precursors, rapid cooling is conducted to drop the temperature to 200° C. If the temperature is left at 300° C., most of the reaction precursors are consumed in nucleus formation, and nuclei of various sizes occur with elapse of the time. Rapid cooling can prevent additional nucleus formation in the reaction solvent.

The reaction solvent is then re-heated to 240° C. and retained at the constant temperature for 240 minutes to grow $ZnO_{0.72}S_{0.28}$. As a result, nano-sized base particles having a particle diameter distribution with a 20 nm center size can be synthesized as illustrated in FIG. 3A.

The particle diameter (distribution) of the base particles can be adjusted by controlling the heating time for the reaction solvent. For example, when the reaction solvent is re-heated to 240° C. and retained at the constant temperature for 180 minutes to grow $ZnO_{0.72}S_{0.28}$, nano-sized base particles having a particle diameter distribution with a 10 nm center size can be synthesized. The particle diameter of $ZnO_{0.72}S_{0.28}$ is preferably 20 nm or less.

Subsequently, the reactor is left to cool naturally to 100° C., and a heat treatment is performed at 100° C. for 1 hour. This stabilizes surfaces of the base particles. After being cooled to room temperature, the reaction solution is combined with butanol, which is an anticoagulant, to prevent aggregation of the base particles, followed by stirring for 10 hours. Purification is conducted by repeating centrifugal separation (4000 rpm, 10 minutes) by alternately using dehydrated methanol that dissolves the solvent (TOPO) and toluene that disperses the base particles. By repeating the centrifugal separation, undesirable raw materials and solvents are completely removed.

As illustrated in FIG. 3B, the $ZnO_{0.72}S_{0.28}$ base particle is etched to form a nano-seed having a (0001) surface (C-plane) as the specified surface. The $ZnO_{0.72}S_{0.28}$ base particles synthesized through the above-described step are in a dispersed state in methanol. Methanol is evaporated to condense the base particles. However, the base particles will aggregate if methanol is completely evaporated; thus, a small amount of methanol is left to remain, and ultrapure water serving as a photoetching solution is added thereto. In order to selectively expose the (0001) surface, which is the specified plane orientation, nitric acid (61 vol %) is added. The blend ratio of the etching solution 21 is ultrapure water:nitric acid (61 vol %)=600:1. Oxygen is bubbled for 5 minutes into this solution maintained at 25° C.

Figure 9:
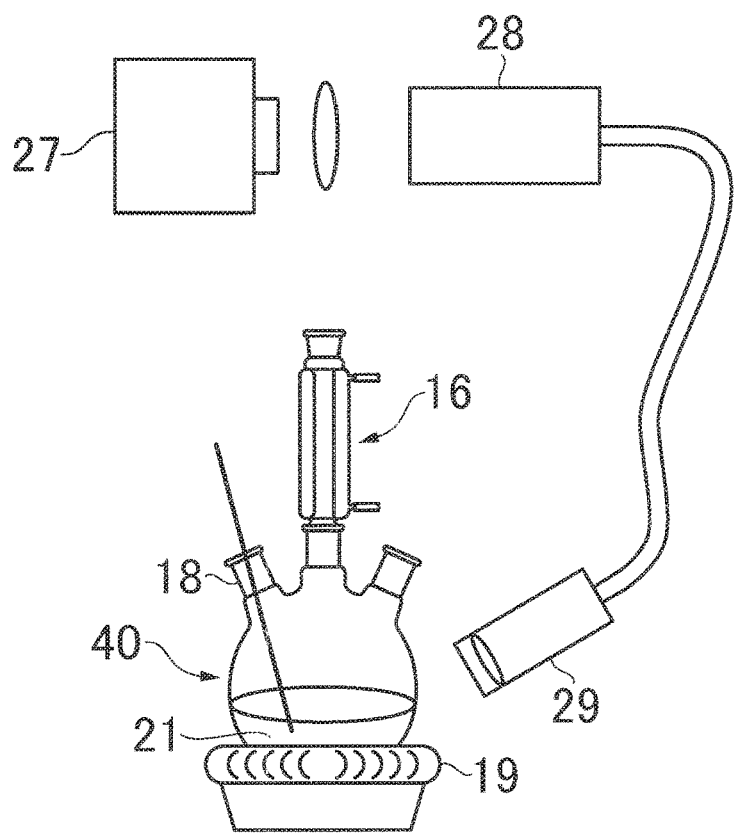
FIG. 9 is a schematic side view of an example of an etching device.

FIG. 9 is a schematic side view illustrating a structure of a photoetching device. Light from a light source 27, such as a mercury lamp, is monochromatized with a monochromator 28 and can be incident on the solution inside the flask 40 through a rod lens 29.

The mixed solution (etching solution) 21 after completion of bubbling is placed in the flask 40. Light having an emission wavelength of 405 nm (3.06 eV) and a half-value width of 6 nm, which is light having a sufficiently shorter wavelength than the absorption edge wavelength of the $ZnO_{0.72}S_{0.28}$ base particle, is applied to the etching solution. Light from a mercury lamp dispersed with the monochromator is used as the light source. The $ZnO_{0.72}S_{0.28}$ base particles having various absorption edge wavelengths due to differences in particle size absorb light and undergo photodissolution reaction, through which the surfaces of the particles dissolve in the photodissolution liquid and the diameter gradually decreases. As etching proceeds, the absorption edge wavelength shifts toward the short wavelength side. In addition, nitric acid, which has a selective etching effect, assists the photoetching, and a (0001) crystal plane appears as a result. The light is applied until the absorption edge wavelength becomes shorter than the wavelength of the applied light and the photodissolution reaction stops. The irradiation time is 20 hours. After completion of etching, thorough washing with water is conducted to completely replace the etching solution. As a result, $ZnO_{0.72}S_{0.28}$ nano-seed particles dominantly having the (0001) surface (C-plane) can be obtained.

The specified surface is not limited to the C-plane. In order to prepare a $ZnO_zS_{1-z}$ nano-seed having an M-plane instead of the C-plane, aqua regia is used as the etching solution. In this case, since the etching rate in the m-axis direction is about 100 times faster than that in the c-axis direction, the surface can be controlled to an M-plane. When off-direction surface control with respect to the C-plane is desirable, a mixed solution of ethylenediaminetetraacetic acid.2Na and ethylenediamine can be used. The nano-seed surface may be modified with surface-modifying groups such as anions, amines, thiols, and organic polymers.

As illustrated in FIG. 3C, an $In_{0.60}Ga_{0.40}N$ layer 13 is grown on the surface of a $ZnO_{0.72}S_{0.28}$ nano-seed 11 having a specified surface, i.e., the C-plane, exposed. Since $In_{0.60}Ga_{0.40}N$ lattice-matches with $ZnO_{0.72}S_{0.28}$, an epitaxial layer having good crystallinity can be grown. The $In_{0.60}Ga_{0.40}N$ layer 13 having a C-plane is grown.

Figure 10A:
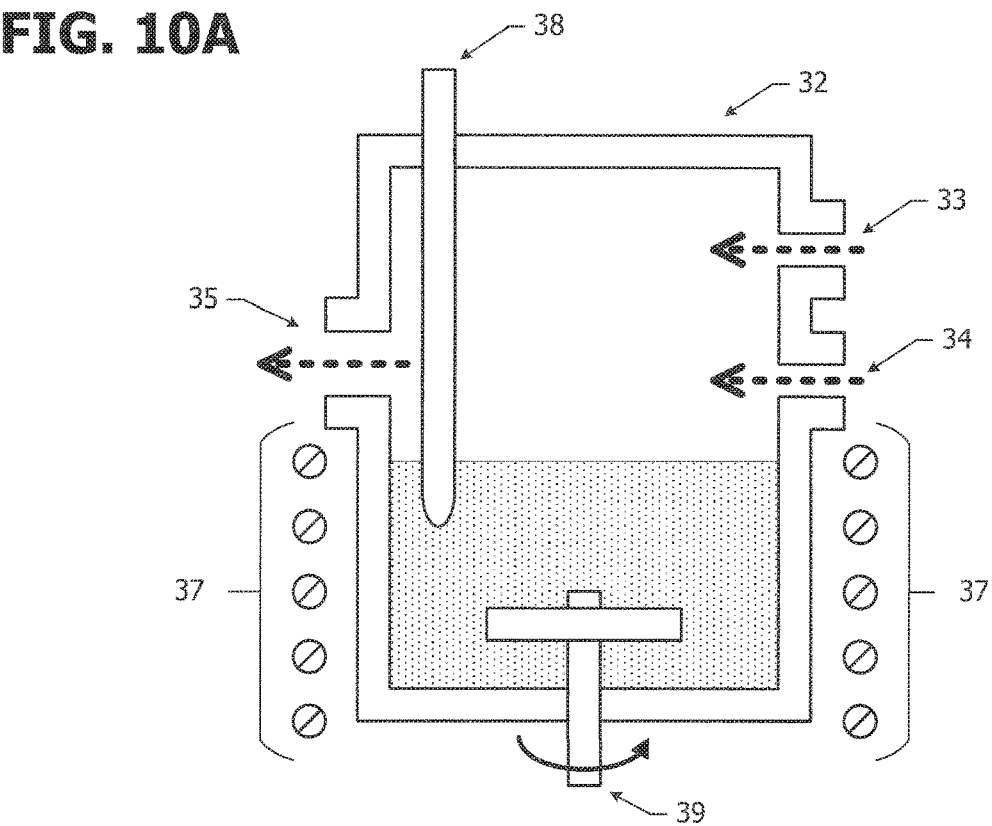
FIGS. 10A and 10B are schematic side views of examples of pressure reactors.

FIG. 10A is a schematic cross-sectional view of an epitaxial growth system, with which pressure is controllable, used in this process.

A reactor 32 into which raw materials are to be placed is formed of stainless steel on the outer side and hastelloy on the inner side. The reactor 32 has at least two air supply ports 33 and 34, and an exhaust port 35.

The air supply ports 33 and 34 are respectively coupled to, for example, an Ar gas supply source and a $N_2$ gas supply source through valves, and Ar gas and $N_2$ gas can be supplied from the air supply ports 33 and 34 to the interior of the reactor 32. A vacuum pump is coupled to the exhaust port 35 through a valve so that the atmosphere (gas) inside the reactor 32 can be evacuated. The partial pressure of each gas in the reactor 32, in particular, the partial pressure of the $N_2$ gas, can be precisely controlled by adjusting the valve.

The reactor 32 is equipped with a temperature sensor 38, a heater 37, a stirring mechanism 39, etc. The temperature sensor 38 can measure the temperature of the content inside the reactor 32. The heater 37 can heat the content. The stirring mechanism 39 (rotary blade) can stir the content.

Six milliliters of an aqueous solution containing the $ZnO_{0.72}S_{0.28}$ nano-seeds 11 that dominantly have the (0001) surface formed in the step illustrated in FIG. 3B is extracted and freeze-dried. Gallium iodide (108 mg, 0.24 mmol), which is a gallium source, indium iodide (165 mg, 0.36 mmol), which is an indium source, sodium amide (500 mg, 12.8 mmol), which is a nitrogen source, and hexadecanethiol (380 μl, 1.0 mmol) and zinc stearate (379 mg, 0.6 mol), which are capping agents, are placed in the reactor 32 containing diphenyl ether (20 ml) serving as a solvent.

The freeze-dried nanoparticles are preliminarily added to the solvent, diphenyl ether, and ultrasonically dispersed. The resulting mixed solution is rapidly heated to 225° C. and retained at 225° C. for 80 minutes. The nitrogen partial pressure during synthesis is adjusted to be 1500 Torr. Then the reactor is again left to cool naturally to 100° C., and a heat treatment is conducted at 100° C. for 1 hour. As a result, the surfaces of the nanoparticles are stabilized.

Subsequently, butanol serving as an anticoagulant is added to the reaction solution cooled to room temperature to prevent aggregation of the nanoparticles followed by stirring for 10 hours. Lastly, purification is conducted by repeating centrifugal separation (4000 rpm, 10 minutes) by alternately using dehydrated methanol that dissolves the solvent (TOPO) and toluene that disperses the nanoparticles. Undesirable raw materials and solvents are completely removed. All operations related to preparation of the sample according to this process are performed inside a glovebox by using vacuum-dried (140° C.) tools and devices.

As illustrated in FIG. 3C, through this procedure, a quantum dot in which the $In_{0.60}Ga_{0.40}N$ nitride semiconductor layer 13 having a thickness of 4.0 nm is epitaxially grown on the C (0001) surface 12 of the $ZnO_{0.72}S_{0.28}$ nano-seed 11 can be obtained. The modifying groups on the surface of the synthesized quantum dot may be substituted with other surface-modifying groups, such as anions, amines, and organic polymers, through ligand exchange. Zinc from zinc stearate serving as a capping agent may mix into InGaN, but this case is also referred to as InGaN.

The thickness of the $In_{0.60}Ga_{0.40}N$ nitride semiconductor layer can be adjusted by controlling the heating time for the mixed solution. The thickness of the $In_{0.60}Ga_{0.40}N$ nitride semiconductor layer may be adjusted while monitoring the wavelength of the light (fluorescence) emitted from the nitride semiconductor layer.

Figure 10B:
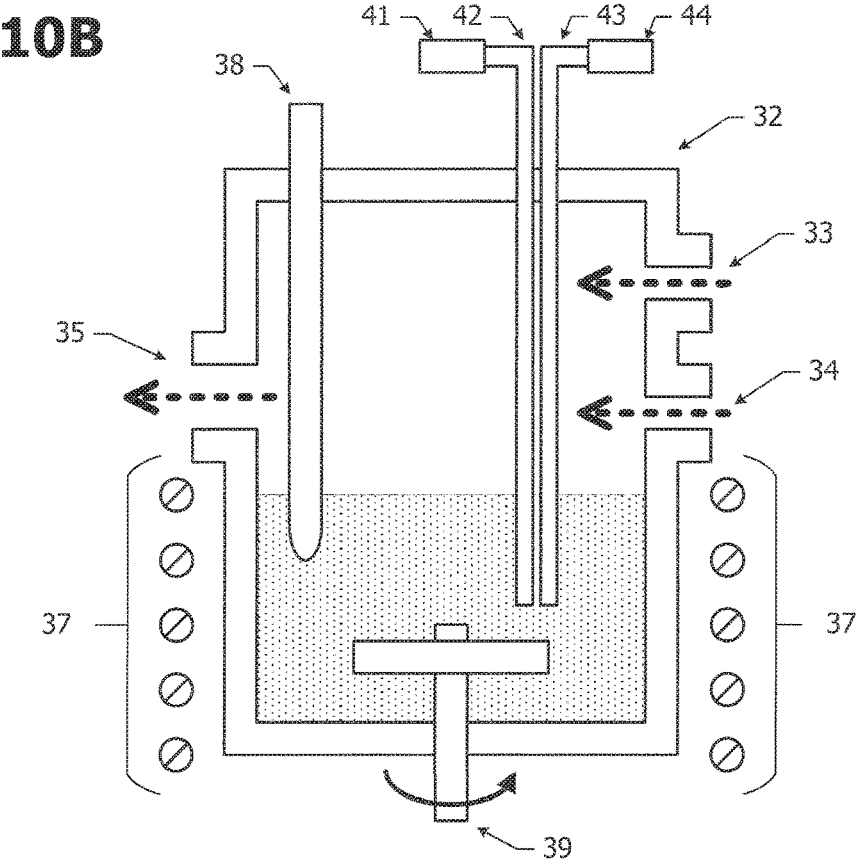

FIG. 10B is a schematic cross-sectional view of another epitaxial growth system that can be used in this process. The growth system may be further equipped with a light source 41, optical fibers 42 and 43, and a photodetector 44 in addition to the structure illustrated in FIG. 10A.

The excited light of a particular wavelength emitted from the light source 41 is applied to the mixed solution (the emission layers dispersed in the mixed solution, i.e., the $In_{0.60}Ga_{0.40}N$ nitride semiconductor layers) through the optical fiber 42. The emission layers dispersed in the mixed solution absorb the excited light and emit light having wavelengths corresponding to their thickness. The light emitted from the emission layer is guided, through the optical fiber 43, into the photodetector 44 having a dispersing function.

As the mixed solution is heated, the thickness of the emission layer increases. When the thickness of the emission layer increases within the range in which the quantum confinement effect is provided, the wavelength of the light emitted therefrom shifts toward the long wavelength side. As soon as the light of the desired wavelength is detected by the photodetector 44, heating of the mixed solution is stopped. The thickness of the emission layer can be adjusted by this method also.

As illustrated in FIG. 3D, an $In_{0.67}Al_{0.33}N$ nitride semiconductor layer 15 is formed on the $In_{0.60}Ga_{0.40}N$ nitride semiconductor layer 13. All operations related to preparation of the sample are performed inside a glovebox by using vacuum-dried (140° C.) tools and devices.

Six milliliters of an aqueous solution containing particles that contain $In_{0.60}Ga_{0.40}N$ layers 13 dominantly having the C (0001) surface is extracted and freeze-dried. Aluminum iodide (80 mg, 0.20 mmol), which is an aluminum source, indium iodide (185 mg, 0.40 mmol), which is an indium source, sodium amide (500 mg, 12.8 mmol), which is a nitrogen source, and hexadecanethiol (380 μl, 1.0 mmol) and zinc stearate (379 mg, 0.6 mol), which are capping agents, are placed in a flask containing diphenyl ether (20 ml) serving as a solvent.

The freeze-dried nanoparticles are preliminarily added to the solvent, diphenyl ether, and ultrasonically dispersed. The resulting mixed solution is rapidly heated to 225° C. and retained at 225° C. for 100 minutes. The nitrogen partial pressure during synthesis is adjusted to be 1500 Torr.

Then the reactor is again left to cool naturally to 100° C., and a heat treatment is conducted at 100° C. for 1 hour. As a result, the surfaces of the nanoparticles are stabilized. Subsequently, butanol serving as an anticoagulant is added to the reaction solution cooled to room temperature to prevent aggregation of the nanoparticles, followed by stirring for 10 hours. Lastly, purification is conducted by repeating centrifugal separation (4000 rpm, 10 minutes) by alternately using dehydrated methanol that dissolves the solvent (diphenyl ether) and toluene that disperses the nanoparticles. By repeating the centrifugal separation, undesirable raw materials and solvents are completely removed.

Through this procedure, a nitride quantum dot in which the $In_{0.67}Al_{0.33}N$ nitride semiconductor layer 15 having a thickness of 5 nm is epitaxially grown on the $In_{0.60}Ga_{0.40}N$ layer 13 can be obtained. The thickness of the $In_{0.67}Al_{0.33}N$ nitride semiconductor layer may be adjusted by controlling the heating time for the mixed solution. Zinc from zinc stearate may mix into InAlN, but this case is also referred to as InAlN.

A nitride quantum dot 51 having an average particle diameter of 12 nm can be formed through the above-described process. The modifying groups on the surface of the synthesized quantum dot may be substituted by other surface-modifying groups, such as anions, amines, and organic polymers, by ligand exchange.

Figure 3E:
FIGS. 3E and 3F are respectively a cross-sectional view and a perspective view schematically illustrating a modification example.

As illustrated in FIG. 3E, the $ZnO_{0.72}S_{0.28}$ nano-seed 11 may be removed. This process is optional. By using an etching solution having different etching rates for the $ZnO_{0.72}S_{0.28}$ nano-seed, the $In_{0.60}Ga_{0.40}N$ layer, and the $In_{0.67}Al_{0.33}N$ layer, $ZnO_{0.72}S_{0.28}$ is selectively etched. Diluted hydrochloric acid that can selectively etch $ZnO_{0.72}S_{0.28}$ is, for example, used as the etching solution. The blend ratio of the etching solution is, for example, hydrochloric acid (36 vol %):pure water=1:100. After completion of etching, thorough washing with water is conducted to completely replace the etching solution.

In order to synthesize nanoparticles having a desired $ZnO_zS_{1-z}$ mixed crystal composition, the ratios of the materials constituting the reaction precursors may be appropriately changed. The lattice mismatch ratio between the nano-seed formed of $ZnO_{0.72}S_{0.28}$ and the $In_{0.60}Ga_{0.40}N$ nitride semiconductor layer is substantially zero. In actual cases, fluctuations due to variation in reaction are allowable. The range of the lattice mismatch may be any range within ±1% when a smaller lattice constant is assumed to be 100%. This can be rewritten into a composition range, $0.67 \leq z \leq 0.78$.

Figure 3F:
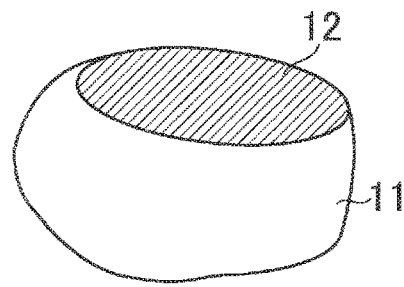

The nano-seed with the specified surface exposed by selective etching has, for example, a plate shape. However, it is sufficient if at least one specified surface is exposed. FIG. 3F illustrates a $ZnO_{0.72}S_{0.28}$ nano-seed 11 having one specified surface 12 exposed.

Although the $ZnO_zS_{1-z}$ mixed crystal composition has been selected as an example of the nano-seed base particle, the material may be any group II-VI semiconductor material, AB (A represents at least one selected from Zn and Mg and B represents at least one element selected from O, S, Se, and Te). For example, ZnOSSe or ZnOSe can be produced by the same procedure by substituting all or some part of bis(trimethylsilyl) sulfide, which is a sulfur-containing material and serves as a material for the seed particle, with a selenium-containing material, tri-n-octylphosphine selenide. Although ZnOS having a wurtzite crystal structure has been selected as an example of the nano-seed base particle, ZnOS having a zinc blende structure may be selected instead.

Furthermore, although an example of using a hot injection method as a method for preparing the nano-seed base particle is described, a solvothermal method that uses reaction in a high-temperature, high-pressure alcohol solvent may be employed, or the nano-seed base particle may be prepared by crushing a bulk member into fine particles (nanosize) by ultrasonic waves and the like. The modifying groups on the surface of the synthesized nano-seed base particle may be substituted with other surface modifying groups, such as anions, amines, thiols, and organic polymers, by ligand exchange.

Second Embodiment

Figure 4A:
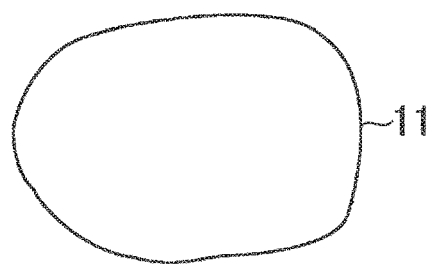
FIGS. 4A to 4E are schematic cross-sectional views of a quantum dot manufacturing process according to a second embodiment.
Figure 4B:
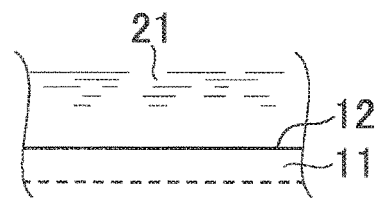
Figure 4C:
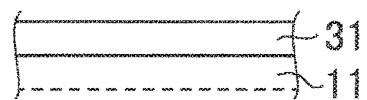
Figure 4D:
Figure 4E:
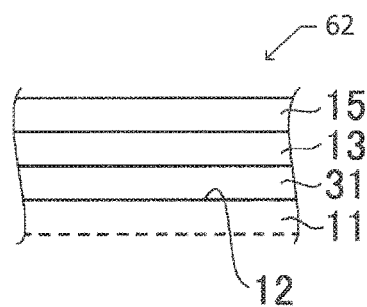

FIG. 4E is a schematic cross-sectional view of a quantum dot 62 according to a second embodiment. For example, an $In_{0.67}Al_{0.33}N$ layer 31 having a (0001) surface, an $In_{0.60}Ga_{0.40}N$ layer 13 having a (0001) surface, and an $In_{0.67}Al_{0.33}N$ layer 15 having a (0001) surface are sequentially stacked on top of each other on a $ZnO_{0.72}S_{0.28}$ nano-seed particle 11 having a specified surface 12, which is a C (0001) surface.

Compared to the quantum dot 61 according to the first embodiment, an $In_{0.67}Al_{0.33}N$ layer 31 is formed between the $ZnO_{0.72}S_{0.28}$ nano-seed particle 11 and the $In_{0.60}Ga_{0.40}N$ layer 13. The $In_{0.67}Al_{0.33}N$ layers 31 and 15 are disposed on both sides of the $In_{0.60}Ga_{0.40}N$ layer 13 so as to constitute a symmetrical structure.

This is a structure in which three layers, namely, the $In_{0.67}Al_{0.33}N$ layer 31, the $In_{0.60}Ga_{0.40}N$ layer 13, and the $In_{0.67}Al_{0.33}N$ layer 15 that have a (0001) surface and lattice-match with the $ZnO_{0.72}S_{0.28}$ nano-seed particle 11 are stacked on the C (0001) surface of the $ZnO_{0.72}S_{0.28}$ nano-seed particle 11. When the $In_{0.60}Ga_{0.40}N$ layer 13 functions as an emission layer, the $In_{0.67}Al_{0.33}N$ layers 31 and 15 on both sides function as barrier layers.

A quantum dot manufacturing method according to the second embodiment will now be described with reference to FIGS. 4A to 4E.

FIG. 4A illustrates a process of synthesizing the $ZnO_{0.72}S_{0.28}$ base particle 11, and FIG. 4B illustrates a process of exposing the specified surface 12 of the base particle 11. These processes are basically the same as the processes of the first embodiment illustrated in FIGS. 3A and 3B, and the description therefor is omitted.

As illustrated in FIG. 4C, an $In_{0.67}Al_{0.33}N$ layer 31 is formed on the nano-seed particle 11 having the C (0001) surface 12 exposed. This is the same process as the process of growing the $In_{0.67}Al_{0.33}N$ layer 15 illustrated in FIG. 3D. All operations related to preparation of the sample are performed inside a glovebox by using vacuum-dried (140° C.) tools and devices.

Six milliliters of an aqueous solution containing the $ZnO_{0.72}S_{0.28}$ nano-seeds 11 dominantly having the C (0001) surface is extracted and freeze-dried. Aluminum iodide (80 mg, 0.20 mmol), which is an aluminum source, indium iodide (185 mg, 0.40 mmol), which is an indium source, sodium amide (500 mg, 12.8 mmol), which is a nitrogen source, and hexadecanethiol (380 µl, 1.0 mmol) and zinc stearate (379 mg, 0.6 mol), which are capping agents, are placed in a flask containing diphenyl ether (20 ml) serving as a solvent. The freeze-dried nanoparticles are preliminarily added to the solvent, diphenyl ether, and ultrasonically dispersed.

The resulting mixed solution is rapidly heated to 225° C. and retained at 225° C. for 40 minutes. The nitrogen partial pressure during synthesis is adjusted to be 1500 Torr. Then the reactor is again left to cool naturally to 100° C., and a heat treatment is conducted at 100° C. for 1 hour. As a result, the surfaces of the nanoparticles are stabilized.

Subsequently, butanol serving as an anticoagulant is added to the reaction solution cooled to room temperature to prevent aggregation of the nanoparticles, followed by stirring for 10 hours. Lastly, purification is conducted by repeating centrifugal separation (4000 rpm, 10 minutes) by alternately using dehydrated methanol that dissolves the solvent (diphenyl ether) and toluene that disperses the nanoparticles. By repeating the centrifugal separation, undesirable raw materials and solvents are completely removed. Thus, an $In_{0.67}Al_{0.33}N$ layer 31 having a thickness of 2.0 nm can be formed on the nano-seed 11.

As illustrated in FIG. 4D, an $In_{0.60}Ga_{0.40}N$ layer 13 is grown on the $In_{0.67}Al_{0.33}N$ layer 31. This process is basically the same as the process illustrated in FIG. 3C in that an $In_{0.60}Ga_{0.40}N$ layer is grown. All operations related to preparation of the sample are performed inside a glovebox by using vacuum-dried (140° C.) tools and devices.

Six milliliters of a methanol dispersion containing quantum dots formed of the $ZnO_{0.72}S_{0.28}$ nano-seeds 11 dominantly having a C (0001) surface and the $In_{0.67}Al_{0.33}N$ layers 31 is extracted and injected to a reactor containing a diphenyl ether (20 ml) serving as a solvent together with gallium iodide (108 mg, 0.24 mmol), which is a gallium source, indium iodide (165 mg, 0.36 mmol), which is an indium source, sodium amide (500 mg, 12.8 mmol), which is a nitrogen source, and hexadecanethiol (380 µl, 1.0 mmol) and zinc stearate (379 mg, 0.6 mol), which are capping agents.

The resulting mixed solution is rapidly heated to 225° C. and retained at 225° C. for 80 minutes. The nitrogen partial pressure during synthesis is adjusted to be 1500 Torr. An $In_{0.60}Ga_{0.40}N$ layer 13 grows as a result.

Then the reactor is again left to cool naturally to 100° C., and a heat treatment is conducted at 100° C. for 1 hour. As a result, the surfaces of the nanoparticles are stabilized. Subsequently, butanol serving as an anticoagulant is added to the reaction solution cooled to room temperature to prevent aggregation of the nanoparticles, followed by stirring for 10 hours. Lastly, purification is conducted by repeating centrifugal separation (4000 rpm, 10 minutes) by alternately using dehydrated methanol that dissolves the solvent (diphenyl ether) and toluene that disperses the nanoparticles. By repeating the centrifugal separation, undesirable raw materials and solvents are completely removed. Through this procedure, a quantum dot in which the $In_{0.60}Ga_{0.40}N$ layer 13 having a thickness of 4.0 nm is formed on the $In_{0.67}Al_{0.33}N$ layer 31 can be obtained.

The modifying groups on the surface of the synthesized quantum dot may be substituted with other surface modifying groups, such as anions, amines, and organic polymers, by ligand exchange.

As illustrated in FIG. 4E, an $In_{0.67}Al_{0.33}N$ layer 15 is formed on the $In_{0.60}Ga_{0.40}N$ layer 13. This process is basically the same as the process for forming the $In_{0.67}Al_{0.33}N$ layer 15 illustrated in FIG. 3D, and the description therefor is omitted. As a result, a quantum dot 52 in which the $In_{0.67}Al_{0.33}N$ 15 having a thickness of 4.0 nm is formed on the $In_{0.60}Ga_{0.40}N$ layer 13 can be obtained.

Figure 4F:
FIG. 4F is a schematic cross-sectional view of a modification example.

FIG. 4F illustrates a process for removing the $ZnO_{0.72}S_{0.28}$ nano-seed. This process is optional. Particles each containing the $ZnO_{0.72}S_{0.28}$ nano-seed 11, the $In_{0.67}Al_{0.33}N$ layer 31, the $In_{0.60}Ga_{0.40}N$ layer 13, and the $In_{0.67}Al_{0.33}N$ layer 15 are in a dispersed state in methanol. Methanol is evaporated to condense the nanoparticles. A small amount of methanol is left to remain.

Then the resulting solution is added to an etching solution having different etching rates for the $ZnO_{0.72}S_{0.28}$ nano-seed, the $In_{0.60}Ga_{0.40}N$ layer, and the $In_{0.67}Al_{0.33}N$ layer so as to etch-away the $ZnO_{0.72}S_{0.28}$ nano-seed. Diluted hydrochloric acid (36 vol %) that can selectively etch the $ZnO_{0.72}S_{0.28}$ nano-seed is used as the etching solution. The blend ratio of the etching solution is hydrochloric acid (36 vol %):pure water=1:100. After completion of etching, thorough washing with water is conducted to completely replace the etching solution. As a result, a nitride quantum dot having an average particle diameter of 12 nm, and formed of a multilayer body that includes the $In_{0.67}Al_{0.33}N$ layer 31, the $In_{0.60}Ga_{0.40}N$ layer 13, and the $In_{0.67}Al_{0.33}N$ layer 15 can be obtained.

Third Embodiment

FIG. 5E is a schematic cross-sectional view of a quantum dot 63 according to a third embodiment. This is a structure in which an $In_{0.67}Al_{0.33}N$ layer 53 (barrier layer) covers a flat-plate-shaped $In_{0.60}Ga_{0.40}N$ layer 13 (emission layer). The flat-plate-shaped $In_{0.60}Ga_{0.40}N$ layer 13 can be deemed to be a core layer, and the $In_{0.67}Al_{0.33}N$ layer 53 can be deemed to be a shell layer.

A quantum dot manufacturing method according to the third embodiment will now be described with reference to FIGS. 5A to 5E.

FIG. 5A illustrates a process for forming an $In_{0.60}Ga_{0.40}N$ layer 13 after the $ZnO_{0.72}S_{0.28}$ base particle 11 is synthesized and the specified surface 12 of the base particle 11 is exposed. These processes are basically the same as the processes of the first embodiment illustrated in FIGS. 3A to 3C, and the description therefor is omitted.

As illustrated in FIG. 5B, a $ZnO_{0.72}S_{0.28}$ layer 51 (seed layer) is grown on the $In_{0.60}Ga_{0.40}N$ layer 13. This process is basically the same as the process illustrated in FIG. 3A in that $ZnO_{0.72}S_{0.28}$ is grown.

Now, FIG. 8 is referred. The syringes 17 respectively filled with reaction precursors, i.e., diethylzinc ($Zn(C_2H_5)_2$) sealed with inert gas, oxygen-bubbled octylamine ($C_8H_{17}NH_2$), and bis(trimethylsilyl) sulfide, are prepared. To obtain 4.0 mmol of diethylzinc, 2.8 mmol of oxygen gas-bubbled octylamine, and 1.2 mmol of bis(trimethylsilyl) sulfide, 410 μl of diethylzinc, 460 μl of octylamine, and 250 μl of bis(trimethylsilyl) sulfide are prepared. Oxygen-bubbled octylamine is prepared in advance by bubbling oxygen into octylamine for 2 minutes.

A methanol dispersion (reaction solvent) containing quantum dots each formed of the $ZnO_{0.72}S_{0.28}$ nano-seed 11 dominantly having a C (0001) surface and the $In_{0.60}Ga_{0.40}N$ layer 13 is placed in a reactor 40. An inert gas (Ar) atmosphere is created, and the dispersion is heated to 300° C. with the heating mantle 19 while being stirred with a stirrer.

As soon as the reaction solvent reaches 300° C., the reaction precursors are quickly injected from the respective syringes. Immediately after injection of the reaction precursors, rapid cooling is conducted to drop the temperature to 200° C. The reaction solvent is then re-heated to 240° C. and retained at the constant temperature for 20 minutes to grow $ZnO_{0.72}S_{0.28}$. As a result, the $ZnO_{0.72}S_{0.28}$ layer 51 having a thickness of 2.0 nm as illustrated in FIG. 5B can be formed. The $ZnO_{0.72}S_{0.28}$ layer 51 dominantly has a C (0001) surface.

Subsequently, the reactor is left to cool naturally to 100° C., and a heat treatment is performed at 100° C. for 1 hour. After being cooled to room temperature, the reaction solution is combined with butanol, which is an anticoagulant, followed by stirring for 10 hours. Purification is conducted by repeating centrifugal separation (4000 rpm, 10 minutes) by alternately using dehydrated methanol and toluene.

As illustrated in FIG. 5C, an $In_{0.60}Ga_{0.40}N$ layer 13a layer is again grown on the $ZnO_{0.72}S_{0.28}$ layer 51. This process is basically the same as the process for forming the $In_{0.60}Ga_{0.40}N$ layer 13 illustrated in FIG. 3C (or FIG. 5A), and the description therefor is omitted. Note that after forming the $In_{0.60}Ga_{0.40}N$ layer 13a, a $ZnO_{0.72}S_{0.28}$ layer (seed layer) and an $In_{0.60}Ga_{0.40}N$ layer (emission layer) may further be formed.

As illustrated in FIG. 5D, the $ZnO_{0.72}S_{0.28}$ nano-seed 11 and the seed layer 51 are removed. This process is basically the same as the process for removing $ZnO_{0.72}S_{0.28}$ illustrated in FIGS. 3E and 4F.

The particles each containing the $ZnO_{0.72}S_{0.28}$ nano-seed 11, the $In_{0.60}Ga_{0.40}N$ layer 13, the $ZnO_{0.72}S_{0.28}$ seed layer 51, and the $In_{0.60}Ga_{0.40}N$ layer 13a are in a dispersed state in methanol. Methanol is evaporated to condense the nanoparticles. A small amount of methanol is left to remain.

Then the resulting solution is added to an etching solution having different etching rates for $ZnO_{0.72}S_{0.28}$ (nano-seed 11 and seed layer 51) and $In_{0.60}Ga_{0.40}N$ (emission layers 13 and 13a) so as to etch away $ZnO_{0.72}S_{0.28}$. Diluted hydrochloric acid that can selectively etch $ZnO_{0.72}S_{0.28}$ is used as the etching solution. The blend ratio of the etching solution is, for example, hydrochloric acid (36 vol %):pure water=1:100. After completion of etching, thorough washing with water is conducted to completely replace the etching solution. As a result, the $In_{0.60}Ga_{0.40}N$ layers 13 and 13a separate, and single-layer bodies respectively formed of $In_{0.60}Ga_{0.40}N$ layers 13 and 13a can be obtained.

As illustrated in FIG. 5E, each of the single-layer bodies, $In_{0.60}Ga_{0.40}N$ layers 13 and 13a, is coated with an $In_{0.67}Al_{0.33}N$ layer 53. This process is basically the same as the process for forming the $In_{0.67}Al_{0.33}N$ layers 15 and 31 illustrated in FIGS. 3D and 4C in that $In_{0.67}Al_{0.33}N$ is grown.

Six milliliters of an aqueous solution containing the single-layer bodies, $In_{0.60}Ga_{0.40}N$ layers 13 and 13a, dominantly having the (0001) surface is extracted and freeze-dried. Aluminum iodide (80 mg, 0.20 mmol), which is an aluminum source, indium iodide (185 mg, 0.40 mmol), which is an indium source, sodium amide (500 mg, 12.8 mmol), which is a nitrogen source, and hexadecanethiol (380 μl, 1.0 mmol) and zinc stearate (379 mg, 0.6 mol), which are capping agents, are placed in a flask containing diphenyl ether (20 ml) serving as a solvent. The freeze-dried nanoparticles are preliminarily added to the solvent, diphenyl ether, and ultrasonically dispersed.

The resulting mixed solution is rapidly heated to 225° C. and retained at 225° C. for 100 minutes. The nitrogen partial pressure during synthesis is adjusted to be 1500 Torr. Then the reactor is again left to cool naturally to 100° C., and a heat treatment is conducted at 100° C. for 1 hour.

Subsequently, butanol serving as an anticoagulant is added to the reaction solution cooled to room temperature, followed by stirring for 10 hours. Lastly, purification is conducted by repeating centrifugal separation (4000 rpm, 10 minutes) by alternately using dehydrated methanol that dissolves the solvent (diphenyl ether) and toluene that disperses the nanoparticles. As a result, an $In_{0.67}Al_{0.33}N$ layer 53 having a thickness of 5 nm and covering the $In_{0.60}Ga_{0.40}N$ layer 13 or 13a can be formed.

In the manufacturing methods according to the first embodiment and the second embodiment, the number of emission layers provided on one nano-seed particle is one (single layer). However, in the manufacturing method according to the third embodiment, the number of emission layers provided on one nano-seed particle is two (or more than two). Since it is considered that the planar size of the emission layers provided on the same nano-seed particle is substantially the same, the overall variation in planar size of the emission layers is considered to be less in the manufacturing method according to the third embodiment. In the manufacturing methods of the embodiments, the step of exposing a specified crystal plane of a seed particle (the step illustrated in FIG. 3B, 4B, or 5A) takes a particularly long time and more efforts; thus, the manufacturing method according to the third embodiment with which a larger number of emission layers can be obtained in one step of processing (photo-etching) the nano-seed particles can be considered to be more productive and efficient.

Fourth Embodiment

Figure 6A:
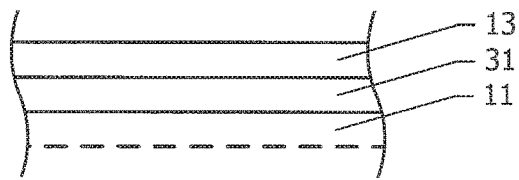
FIGS. 6A to 6E are schematic cross-sectional views of a quantum dot manufacturing process according to a fourth embodiment.
Figure 6B:
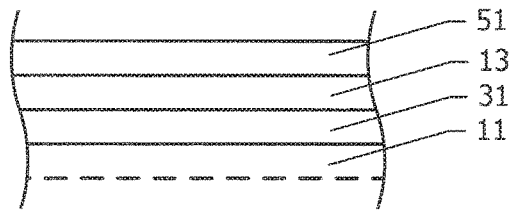
Figure 6C:
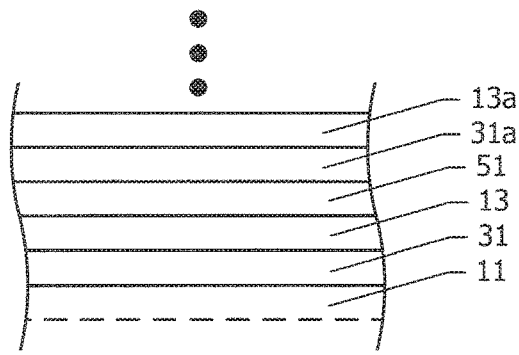
Figure 6D:
Figure 6D:
Figure 6E:
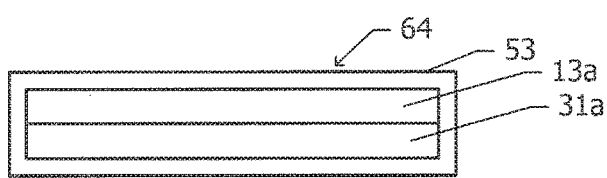
Figure 6E:
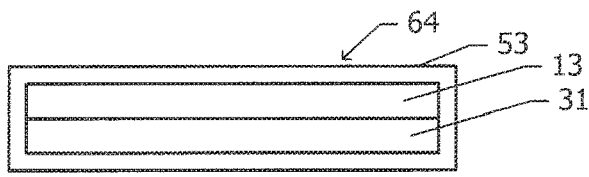

FIG. 6E is a schematic cross-sectional view of a quantum dot 64 according to a fourth embodiment. The quantum dot has a structure in which a flat-plate-shaped multilayer body formed of an $In_{0.67}Al_{0.33}N$ layer 31 and an $In_{0.60}Ga_{0.40}N$ layer 13 is covered with an $In_{0.67}Al_{0.33}N$ layer 53. The multilayer body that includes the $In_{0.67}Al_{0.33}N$ layer 31 and the $In_{0.60}Ga_{0.40}N$ layer 13 can be deemed to be a core layer, and the $In_{0.67}Al_{0.33}N$ layer 53 can be deemed to be a shell layer.

Compared to the quantum dot 63 according to the third embodiment, the core layer has a two-layer structure that includes the $In_{0.67}Al_{0.33}N$ layer 31 and the $In_{0.60}Ga_{0.40}N$ layer 13. Because the $In_{0.67}Al_{0.33}N$ layer 31 is provided, the thickness of the overall shell layer (barrier layer) including the $In_{0.67}Al_{0.33}N$ layer 53 can be made more uniform.

A quantum dot manufacturing method according to the fourth embodiment will now be described with reference to FIGS. 6A to 6E.

FIG. 6A illustrates a process of forming a multilayer body that includes the $In_{0.67}Al_{0.33}N$ layer 31 and the $In_{0.60}Ga_{0.40}N$ layer 13 after synthesizing the $ZnO_{0.72}S_{0.28}$ base particle 11 and exposing the specified surface 12 of the base particle 11. This process is basically the same as the process of the second embodiment illustrated in FIGS. 4A to 4D, and the description therefor is omitted.

As illustrated in FIG. 6B, a $ZnO_{0.72}S_{0.28}$ layer 51 (seed layer) is formed on the $In_{0.60}Ga_{0.40}N$ layer 13. This process is basically the same as the process for forming the $ZnO_{0.72}S_{0.28}$ layer 51 illustrated in FIG. 5B, and the description therefor is omitted.

As illustrated in FIG. 6C, the $In_{0.67}Al_{0.33}N$ layer 31a and the $In_{0.60}Ga_{0.40}N$ layer 13a are again grown on the $ZnO_{0.72}S_{0.28}$ layer 51. This process is basically the same as the process for forming the $In_{0.67}Al_{0.33}N$ layer 31 and the $In_{0.60}Ga_{0.40}N$ layer 13 illustrated in FIGS. 4C and 4D (and FIG. 6A), and the description therefor is omitted. Note that, after the $In_{0.60}Ga_{0.40}N$ layer 13a is formed, a $ZnO_{0.72}S_{0.28}$ layer (seed layer) and a multilayer body that includes an $In_{0.67}Al_{0.33}N$ layer and an $In_{0.60}Ga_{0.40}N$ layer may be further formed.

As illustrated in FIG. 6D, the $ZnO_{0.72}S_{0.28}$ nano-seed 11 and the seed layer 51 are removed. This process is basically the same as the process of removing $ZnO_{0.72}S_{0.28}$ illustrated in FIG. 5D, and the description therefor is omitted. A multilayer body that includes an $In_{0.67}Al_{0.33}N$ layer 31 or 31a and an $In_{0.60}Ga_{0.40}N$ layer 13 or 13a can be obtained.

As illustrated in FIG. 6E, the multilayer body including the $In_{0.67}Al_{0.33}N$ layer 31 or 31a and the $In_{0.60}Ga_{0.40}N$ layer 13 or 13a is covered with an $In_{0.67}Al_{0.33}N$ layer 53. This process is basically the same as the $In_{0.67}Al_{0.33}N$ covering process illustrated in FIG. 5E, and the description therefor is omitted.

Fifth Embodiment

Figure 7A:
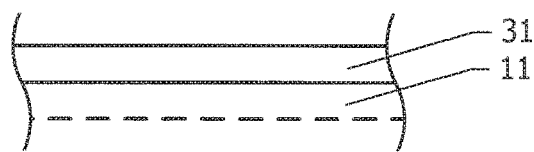
FIGS. 7A to 7D are schematic cross-sectional views of a quantum dot manufacturing process according to a fifth embodiment.
Figure 7B:
Figure 7C:
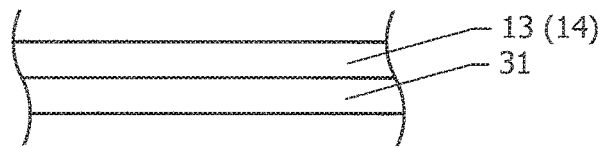
Figure 7D:
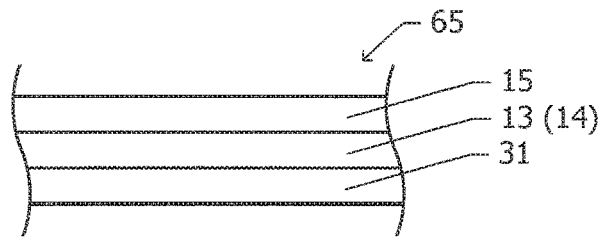

FIG. 7D is a schematic cross-sectional view of a quantum dot 65 according to a fifth embodiment. This has the same structure as the quantum dot illustrated in FIG. 4F. That is, the quantum dot has a three-layer multilayer structure that includes an $In_{0.67}Al_{0.33}N$ layer 31, an $In_{0.60}Ga_{0.40}N$ layer 13, and an $In_{0.67}Al_{0.33}N$ layer 15. When the $In_{0.60}Ga_{0.40}N$ layer 13 functions as an emission layer, the $In_{0.67}Al_{0.33}N$ layers 31 and 15 on both sides function as barrier layers.

A quantum dot manufacturing method according to the fifth embodiment will now be described with reference to FIGS. 7A to 7D.

FIG. 7A illustrates a process of forming an $In_{0.67}Al_{0.33}N$ layer 31 after synthesizing the $ZnO_{0.72}S_{0.28}$ base particle 11 and exposing the specified surface 12 of the base particle 11. This process is basically the same as the process of the second embodiment illustrated in FIG. 4A to 4C, and the description therefor is omitted.

The largest width within the specified surface 12 of the nano-seed 11 is, for example, about 7 nm. The particle diameter and the longest width within the specified surface 12 of the nano-seed 11 are preferably 20 nm or less.

The thickness of the $In_{0.67}Al_{0.33}N$ layer 31 is about 2.0 nm. This thickness is enough for providing a quantum confinement effect.

As illustrated in FIG. 7B, the $ZnO_{0.72}S_{0.28}$ nano-seed 11 is removed. This process is basically the same as the process of removing $ZnO_{0.72}S_{0.28}$ illustrated in FIG. 4F (or FIG. 5D or 6D), and the description therefor is omitted. As a result, a single-layer body, $In_{0.67}Al_{0.33}N$ layer 31, is obtained.

As illustrated in FIG. 7C, an $In_{0.60}Ga_{0.40}N$ layer 13 is grown on the $In_{0.67}Al_{0.33}N$ layer 31. This process is basically the same as the process of growing the $In_{0.60}Ga_{0.40}N$ layer 13 illustrated in FIG. 4D, and the description therefor is omitted. As a result, a quantum dot in which the $In_{0.60}Ga_{0.40}N$ layer 13 having a thickness of 4.0 nm is formed on the $In_{0.67}Al_{0.33}N$ layer 31 can be obtained. This thickness is enough for providing a quantum confinement effect.

As illustrated in FIG. 7D, an $In_{0.67}Al_{0.33}N$ layer 15 is formed on the $In_{0.60}Ga_{0.40}N$ layer 13. This process is basically the same as the process of forming the $In_{0.67}Al_{0.33}N$ layer 15 illustrated in FIG. 4E (or FIG. 3D), and the description therefor is omitted. As a result, a quantum dot in which the $In_{0.67}Al_{0.33}N$ layer 15 having a thickness of 2.0 nm is formed on the $In_{0.60}Ga_{0.40}N$ layer 13 can be obtained.

The timing of removing the nano-seed 11 may be any time after formation of the $In_{0.67}Al_{0.33}N$ layer 31. For example, the nano-seed 11 may be removed after formation of the $In_{0.60}Ga_{0.40}N$ layer 13 or after formation of the $In_{0.67}Al_{0.33}N$ layer 15.

The $In_{0.67}Al_{0.33}N$ layer 31 (first barrier layer) and the $In_{0.67}Al_{0.33}N$ layer 15 (second barrier layer) have a wider bandgap than the $In_{0.60}Ga_{0.40}N$ layer 13 (first emission layer), and a quantum confinement effect (one-dimensional quantum confinement effect) occurs in the first emission layer 13 in at least the thickness direction. In the fifth embodiment, the thickness of the first emission layer 13 is about 4 nm, and the wavelength of the light emitted therefrom is about 550 nm.

The size of the first emission layer 13 (and the first and second barrier layers 31 and 15) in the planar direction is defined by the size of the specified surface 12 of the nano-seed 11. The thickness of the first emission layer 13 is easily adjustable (by controlling the heating time for the mixed solution in the step of growing the $In_{0.60}Ga_{0.40}N$ layer 13). That is, the size of the first emission layer 13 can be one-dimensionally (only in the thickness direction) adjusted. Since the largest width within the specified surface 12 of the nano-seed 11 is preferably 20 nm or less, the largest width of the first emission layer 13 (and the first and second barrier layers 31 and 15) in the in-plane direction is also preferably 20 nm or less.

Figure 7E:
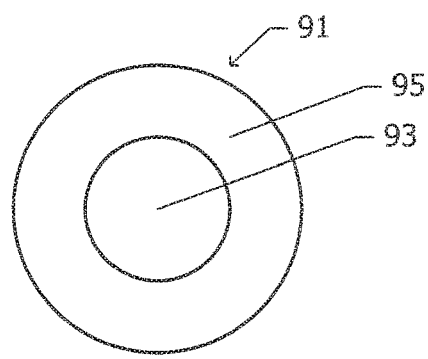
FIG. 7E is a schematic cross-sectional view of a quantum dot according to a reference example.

FIG. 7E illustrates a quantum dot 91 according to a reference example. The quantum dot 91 has a core-shell structure, and includes a spherical core 93 that has a light-emitting property, and a shell layer 95 that covers the core 93 and has a wider bandgap than the core 93. A (three-dimensional) quantum confinement effect supposedly occurs in the core 93. The size of the spherical core 93 is difficult to control one-dimensionally and typically controlled three-dimensionally by changing the particle size (diameter). The emission layer ($In_{0.60}Ga_{0.40}N$ layer 13) of the embodiments can be deemed to correspond to the core of the reference example, and the barrier layer ($In_{0.67}Al_{0.33}N$ layer 15 or 31) of the embodiments can be deemed to correspond to the shell layer of the reference example.

In the fifth embodiment, the size of the emission layer 13 can be adjusted only one-dimensionally (only in the thickness direction). Thus, precise adjustment of the size of the emission layer 13 is relatively easy, and it is possible to more precisely control the bandgap and emission wavelength of the emission layer 13. Meanwhile, in the reference example, the size of the core 93 can only be adjusted three-dimensionally. Thus, it is relatively difficult to precisely control the size of the core 93, and it is difficult to precisely control the bandgap and emission wavelength of the core 93.

The combination of the $In_{0.67}Al_{0.33}N$ layers 31 and 15 that function as barrier layers and the $In_{0.60}Ga_{0.40}N$ layer 13 that functions as an emission layer constitutes a type-I band off-set structure. A type-I band off-set structure has a structure in which a layer ($In_{0.60}Ga_{0.40}N$ layer) with a narrow bandgap is sandwiched by layers ($In_{0.67}Al_{0.33}N$ layers) with wide bandgaps, and carrier recombination can occur inside the layer with a narrow bandgap.

The $In_{0.60}Ga_{0.40}N$ layer that functions as an emission layer can be replaced by a $ZnO_{0.72}S_{0.28}$ layer. The combination of the $In_{0.67}Al_{0.33}N$ layer and the $ZnO_{0.72}S_{0.28}$ layer constitutes a type-II band off-set structure. In the type-II band off-set structure, carrier recombination can occur between adjacent layers.

A modification example of the quantum dot manufacturing method according to the fifth embodiment will now be described. In this modification example, the $In_{0.60}Ga_{0.40}N$ layer 13 of the quantum dot illustrated in FIG. 7D is replaced by a $ZnO_{0.72}S_{0.28}$ layer 14.

As in the process illustrated in FIG. 7A, after a $ZnO_{0.72}S_{0.28}$ base particle 11 is synthesized and the specified surface 12 of the base particle 11 is exposed, an $In_{0.67}Al_{0.33}N$ layer 31 is formed. Then, as in the process illustrated in FIG. 7B, the $ZnO_{0.72}S_{0.28}$ nano-seed 11 is removed to obtain a single-layer body, $In_{0.67}Al_{0.33}N$ layer 31.

Subsequently, as illustrated in FIG. 7C, a $ZnO_{0.72}S_{0.28}$ layer 14 is grown on the $In_{0.67}Al_{0.33}N$ layer 31. This process is basically the same as the process illustrated in FIGS. 3A and 4A in that a $ZnO_{0.72}S_{0.28}$ layer is grown.

FIG. 8 is now referred. A methanol dispersion (reaction solvent) containing single-layer bodies, $In_{0.67}Al_{0.33}N$ layers 31, dominantly having the (0001) surface is placed in the reactor 40. An inert gas (Ar) atmosphere is created, and the dispersion is heated to 300° C. with the heating mantle 19 while being stirred with a stirrer.

As soon as the reaction solvent reaches 300° C., the reaction precursors (diethylzinc, octylamine, and bis(trimethylsilyl) sulfide) are quickly injected from the respective syringes 17. Due to pyrolysis of the reaction precursors, crystal nuclei of $ZnO_{0.72}S_{0.28}$ are generated. Immediately after injection of the reaction precursors, rapid cooling is conducted to drop the temperature to 200° C. The reaction solvent is then re-heated to 240° C. and retained at the constant temperature for 70 minutes to grow $ZnO_{0.72}S_{0.28}$. As a result, the $ZnO_{0.72}S_{0.28}$ layer 14 having a thickness of 7.0 nm is synthesized. The $ZnO_{0.72}S_{0.28}$ layer 14 dominantly has a C (0001) surface.

The thickness of the $ZnO_{0.72}S_{0.28}$ layer can be adjusted by controlling the heating time for the reaction solvent. For example, when the reaction solvent is re-heated to 240° C. and retained at the constant temperature for 50 minutes to grow $ZnO_{0.72}S_{0.28}$, a $ZnO_{0.72}S_{0.28}$ layer 14 having a thickness of 5.0 nm can be formed.

Subsequently, the reactor is left to cool naturally to 100° C., and a heat treatment is performed at 100° C. for 1 hour. After being cooled to room temperature, the reaction solution is combined with butanol, which is an anticoagulant, to prevent aggregation of $ZnO_{0.72}S_{0.28}$, followed by stirring for 10 hours. Purification is conducted by repeating centrifugal separation (4000 rpm, 10 minutes) by alternately using dehydrated methanol and toluene.

Subsequently, as illustrated in FIG. 7D, an $In_{0.67}Al_{0.33}N$ layer 15 is grown on the $ZnO_{0.72}S_{0.28}$ layer 14. This process is basically the same as the process illustrated in FIG. 4C in that an $In_{0.67}Al_{0.33}N$ layer is grown on the C (0001) surface of $ZnO_{0.72}S_{0.28}$. The process is also basically the same as the process illustrated in FIG. 3D (or FIG. 4E) in that an $In_{0.67}Al_{0.33}N$ layer is grown.

Six milliliters of an aqueous solution containing the quantum dots each formed of the $In_{0.67}Al_{0.33}N$ layer 31 and the $ZnO_{0.72}S_{0.28}$ layer 14 is extracted and freeze-dried. Aluminum iodide (80 mg, 0.20 mmol), which is an aluminum source, indium iodide (185 mg, 0.40 mmol), which is an indium source, sodium amide (500 mg, 12.8 mmol), which is a nitrogen source, and hexadecanethiol (380 µl, 1.0 mmol) and zinc stearate (379 mg, 0.6 mol), which are capping agents, are placed in a flask containing diphenyl ether (20 ml) serving as a solvent. The freeze-dried nanoparticles are preliminarily added to the solvent, diphenyl ether, and ultrasonically dispersed.

The resulting mixed solution is rapidly heated to 225° C. and retained at 225° C. for 40 minutes. The nitrogen partial pressure during synthesis is adjusted to be 1500 Torr. Then the reactor is again left to cool naturally to 100° C., and a heat treatment is conducted at 100° C. for 1 hour.

Subsequently, butanol serving as an anticoagulant is added to the reaction solution cooled to room temperature, followed by stirring for 10 hours. Lastly, purification is conducted by repeating centrifugal separation (4000 rpm, 10 minutes) by alternately using dehydrated methanol and toluene that disperses the nanoparticles. As a result, an $In_{0.67}Al_{0.33}N$ layer 15 having a thickness of 2.0 nm can be formed on the $ZnO_{0.72}S_{0.28}$ layer 14.

When the thickness of each of the $In_{0.67}Al_{0.33}N$ layers 31 and 15 is about 2 nm and the thickness of the $ZnO_{0.72}S_{0.28}$ layer 14 is about 7 nm, the emission wavelength is about 2.9 µm. When the thickness of the $ZnO_{0.72}S_{0.28}$ layer 14 is about 5 nm, the emission wavelength is about 2.5 µm.

Sixth Embodiment

Figure 7F:
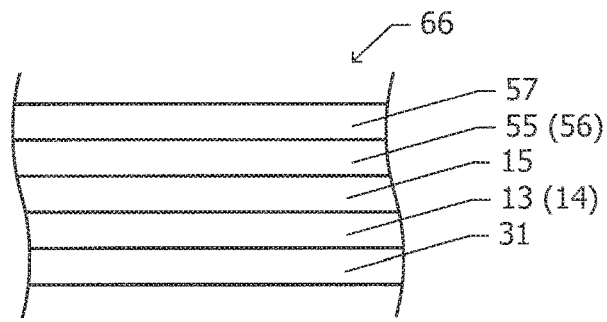
FIG. 7F is a schematic cross-sectional view of a quantum dot according to a sixth embodiment.

FIG. 7F is a schematic cross-sectional view of a quantum dot 66 according to a sixth embodiment. This is obtained by further stacking an $In_{0.60}Ga_{0.40}N$ layer 55 (second emission layer) and an $In_{0.67}Al_{0.33}N$ layer 57 (third barrier layer) on the quantum dot 65 according to the fifth embodiment illustrated in FIG. 7D. The process for growing the $In_{0.60}Ga_{0.40}N$ layer 55 and the $In_{0.67}Al_{0.33}N$ layer 57 is basically the same as that of the fifth embodiment illustrated in FIGS. 7C and 7D. Alternatively, an emission layer and a barrier layer may be further stacked to manufacture a quantum dot that includes three or more emission layers.

The multilayer body (first flat multilayer structure) that includes the first barrier layer 31, the first emission layer 13, and the second barrier layer 15 constitutes one emission unit. The multilayer body (second flat multilayer structure) that includes the second barrier layer 15, the second emission layer 55, and the third barrier layer 57 constitutes another emission unit. The second barrier layer 15 and the third barrier layer 57 have a wider bandgap than the second emission layer 55. A quantum confinement effect (one-dimensional quantum confinement effect) occurs in the second emission layer 55 in at least the thickness direction.

When the thickness of the second emission layer 55 is equal to the thickness (4 nm) of the first emission layer 13, the emission intensity (wavelength: 550 nm) can be ideally made twice as large as the emission intensity of the quantum dot 65 (FIG. 7D). When the thickness (for example, 5 nm) of the second emission layer 55 is different from the thickness (4 nm) of the first emission layer 13, light of multiple wavelengths (wavelength of 550 nm and wavelength of 630 nm) can be emitted.

As a modification example of the quantum dot 66, the $In_{0.60}Ga_{0.40}N$ layers 13 and 55 that function as emission layers may be respectively replaced by $ZnO_{0.72}S_{0.28}$ layers 14 and 56. For example, when the thickness of each of the barrier layers 31, 15, and 57 formed of $In_{0.67}Al_{0.33}N$ layers is 2 nm and when the thickness of the $ZnO_{0.72}S_{0.28}$ layer 14 and the thickness of the $ZnO_{0.72}S_{0.28}$ layer 56 are, respectively, 5 nm and 7 nm, 2.5 μm light and 2.9 μm light (infrared) can be emitted.

Although the present invention has been described with reference to embodiments, the present invention is not limited by these embodiments. The range of lattice matching indicated in the embodiments is merely illustrative, and multilayer structures can be freely combined as long as the content is adjusted to achieve lattice matching. Moreover, various components and materials may be appropriately changed depending on the manufacturing conditions, usage of quantum dots, etc. It is obvious for a person skilled in the art that various other alterations, improvements, combinations, etc., are possible.

What are claimed are:

1. A quantum dot manufacturing method comprising:
   (a) dispersing, in a solvent, nano-seed particles whose crystal planes are exposed; and
   (b) growing flat-plate-shaped first nitride semiconductor layers epitaxially on the exposed crystal planes of the nano-seed particles in the solvent, the first nitride semiconductor layers being made of $In_x(Al_mGa_n)_{1-x}N$ ($0.15 \leq x \leq 1.0$, m+n=1.0).

2. The quantum dot manufacturing method according to claim 1, wherein the step (a) comprises:
   (a1) preparing base particles made of group II-VI semiconductor material containing Zn or Mg as group II element; and
   (a2) forming the nano-seed particles by etching the base particles in liquid phase.

3. The quantum dot manufacturing method according to claim 2, wherein, in the substep (a2), the base particles are etched by a selective photoetching process.

4. The quantum dot manufacturing method according to claim 3, wherein the nano-seed particles are formed by etching the base particles with an etching solution containing nitric acid, C-planes of the nano-seed particles being exposed.

5. The quantum dot manufacturing method according to claim 3, wherein the nano-seed particles are formed by etching the base particles with an etching solution containing aqua regia, M-planes of the nano-seed particles being exposed.

6. The quantum dot manufacturing method according to claim 2, wherein, in the substep (a2), each crystal plane of the nano-seed particles has a maximum width in an in-plane direction of 20 nm or less.

7. The quantum dot manufacturing method according to claim 2, wherein, in the substep (a1), the base particles contain ZnOS.

8. The quantum dot manufacturing method according to claim 1, wherein, in the step (b), second nitride semiconductor layers made of $In_y(Al_pGa_q)_{1-y}N$ ($0.15 \leq y \leq 1.0$, p+q=1.0) and having different composition from the first nitride semiconductor layers are epitaxially grown on the first nitride semiconductor layers.

9. The quantum dot manufacturing method according to claim 8, wherein, in the step (b), third nitride semiconductor layers having the same composition as the first nitride semiconductor layers are epitaxially grown on the second nitride semiconductor layers.

10. The quantum dot manufacturing method according to claim 1, wherein, in the step (b), first semiconductor layers, seed layers having the same composition as the nano-seed particles, and second semiconductor layers are sequentially epitaxially grown on the crystal planes of the nano-seed particles,
    wherein the method further comprises (c) removing the nano-seed particles and the seed layers to separate the first and second semiconductor layers from each other, and
    wherein the first semiconductor layers include the first nitride semiconductor layers made of $In_x(Al_mGa_n)_{1-x}N$ ($0.15 \leq x \leq 1.0$, m+n=1.0).

11. The quantum dot manufacturing method according to claim 10, further comprising (d) covering each of the first and second semiconductor layers, which are separated from each other, with third semiconductor layers.

12. The quantum dot manufacturing method according to claim 11, wherein each of the second semiconductor layers includes a layer having a composition corresponding to the first nitride semiconductor layers made of $In_x(Al_mGa_n)_{1-x}N$ ($0.15 \leq x \leq 1.0$, m+n=1.0).

13. The quantum dot manufacturing method according to claim 12, wherein each of the first and second semiconductor layers further includes a second nitride semiconductor layer made of $In_y(Al_pGa_q)_{1-y}N$ ($0.15 \leq y \leq 1.0$, p+q=1.0) and having different composition from the first nitride semiconductor layer.

14. The quantum dot manufacturing method according to claim 13, wherein the third semiconductor layer has the same composition as the first nitride semiconductor layers.

15. The quantum dot manufacturing method according to claim 1, wherein in the step (b), first semiconductor layers having plate shapes with thicknesses such that a quantum confinement effect occurs are epitaxially grown on the crystal planes of the nano-seed particles,
    wherein the method further comprises:
    (c) removing the nano-seed particles after growing the first semiconductor layer; and
    (d) sequentially epitaxially growing second and third semiconductor layers, having plate shapes with thicknesses such that a quantum confinement effect occurs, on main surfaces of the first semiconductor layers, and
    wherein the first semiconductor layers include the first nitride semiconductor layers made of $In_x(Al_mGa_n)_{1-x}N$ ($0.15 \leq x \leq 1.0$, m+n=1.0).

* * * * *